United States Patent
Svenson

[11] Patent Number: 6,165,468
[45] Date of Patent: Dec. 26, 2000

[54] ANTIGENIC CARBOHYDRATE LINKED TO AN IMMUNOGENIC CARRIER

[76] Inventor: Stefan Svenson, Brättnevägen 12, S-122 43 Enskede, Sweden

[21] Appl. No.: 09/147,045

[22] PCT Filed: Mar. 17, 1997

[86] PCT No.: PCT/EP97/01321

§ 371 Date: Sep. 25, 1998

§ 102(e) Date: Sep. 25, 1998

[87] PCT Pub. No.: WO97/35613

PCT Pub. Date: Oct. 2, 1997

[30] Foreign Application Priority Data

Mar. 25, 1996 [SE] Sweden ................................. 9601158

[51] Int. Cl.[7] .......................... A61K 39/00; A61K 39/38; A61K 39/385; A61K 39/116; A61K 39/02
[52] U.S. Cl. .................................. 424/184.1; 424/193.1; 424/194.1; 424/197.11; 424/203.1; 424/234.1; 424/258.1; 424/279.1
[58] Field of Search .............................. 424/184.1, 193.1, 424/194.1, 197.11, 203.1, 234.1, 258.1, 279.1

[56] References Cited

U.S. PATENT DOCUMENTS 5,034,519 7/1991 Beuvery et al. .
5,204,098 4/1993 Szu et al. .
5,370,872 12/1994 Cryz et al. .
5,445,817 8/1995 Schneerson et al. .

FOREIGN PATENT DOCUMENTS

| 0 350 230 | 1/1990 | European Pat. Off. . |
| 0 497 525 | 8/1992 | European Pat. Off. . |
| 0 554 708 | 8/1993 | European Pat. Off. . |
| 86 05098 | 9/1986 | WIPO . |
| 94 04195 | 3/1994 | WIPO . |
| 94 06467 | 3/1994 | WIPO . |

OTHER PUBLICATIONS

Blair et al., Journal of Immunological Methods, 59:129–143 (1983).

*Primary Examiner*—Phuong T. Bui
*Assistant Examiner*—Li Lee
*Attorney, Agent, or Firm*—Bacon & Thomas

[57] ABSTRACT

A general method of producing an immunogenic product consisting of antigenically active carbohydrate moieties (ACM) which each are covalently coupled via identical divalent bridge groups to immunologically active carriers (IAC) containing amino groups, is disclosed. The immunogenic product comprises a divalent bridge group which has structural formula (I). In addition to the immunogenic product, the invention also comprises use of said product as immunizing component.

(I)

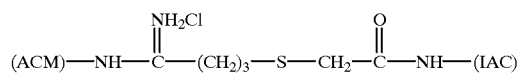

13 Claims, No Drawings

ANTIGENIC CARBOHYDRATE LINKED TO AN IMMUNOGENIC CARRIER

This application is the National Stage Application filed under 35 U.S.C. 371 of PCT/EP97/01321 filed on Mar. 17, 1997.

The present invention relates to a method of producing immunogenic products, which are useful as immunizing components in vaccines. Further, the invention relates to such immunogenic products, and vaccines and vaccine mixtures. The immunogenic products of the invention consist of antigenically active carbohydrate moieties covalently coupled via a newly invented bridge group to immunologically active carriers.

BACKGROUND

Most virulent bacteria have carbohydrates on their surface, such as lipopolysaccharides and capsular polysaccharides. Antibodies directed against capsular polysaccharides provide, among other things, enhanced phagocytosis and killing of bacterial cells. Usually there are a number of serotypes of a given bacterial species, for example there are more than 80 known serotypes of Streptococcus pneumoniae related to their carbohydrate capsular structures.

Bacterial polysaccharides are classical examples of antigens that are not T helper cell-dependent, and hence, if they are immunogenic at all, they mainly induce IgM class of antibodies. This is so, because only B cells respond to them, and B cells cannot mediate the memory function as opposed to the T cells, which also mediate immunological booster effects.

In immunologically immature small children, elderly and immunosuppressed persons polysaccharides are known to be poor immunogens or not at all immunogenic.

Therefore, polysaccharide antigens which are chemically conjugated to carriers comprising T cell epitopes are effective as vaccines also for the above mentioned immunologically immature children and immunosuppressed adults.

The vaccine-producing industry has long been searching for a general method of producing conjugate-type vaccines. A general and simple method to produce such vaccines would not only be more practical but would also make process and quality control easier.

DESCRIPTION OF THE INVENTION

The present invention provides a general method of producing immunogenic products comprising antigenically active carbohydrate moieties and immunologically active carriers, which products are useful as immunizing is components in conjugate-type vaccines.

More specifically the present invention provides a method of producing an immunogenic product consisting of antigenically active carbohydrate moieties (ACM) which are each covalently coupled via identical divalent bridge groups to immunologically active carriers (IAC) containing amino groups, wherein said divalent bridge group has the following structural formula

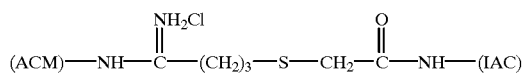

which comprises the steps of reductive amination of antigenically active carbohydrate moieties (ACM) to introduce amino groups on said moieties (ACM—NH$_2$), followed by thiolation of said amino groups with iminothiolane

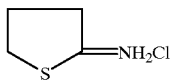

whereupon the so produced thiolated products are covalently coupled to immunologically active carriers (IAC) containing aminogroups activated by treatment with N-hydroxysuccinimide bromoacetate, to produce the desired immunogenic product.

Further, the present invention provides an immunogenic product consisting of antigenically active carbohydrate moieties (ACM) which each are covalently coupled via identical divalent bridge groups to immunologically active carriers (IAC) containing amino groups, wherein said divalent bridge group has the following structural formula

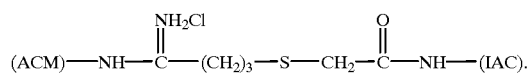

The immunogenic products of the invention is useful as an immunizing component in vaccines.

In a preferred embodiment of the invention the antgenically active carbohydrate moieties (ACM) of the immunogenic products derive from bacterial O-polysaccharides and/or capsular polysaccharides. Specific examples of such saccharides are those which derive from Salmonella serotypes BO and/or DO.

In another preferred embodiment said antigenically active carbohydrate moieties (ACM) derive from different serotypes of *Streptococcus pneumoniae* capsular polysaccharides.

In yet another preferred embodiment said antigenically active carbohydrate moieties (ACM) derive from *Haemophilus influenzae* capsular polysaccharides.

The antigenically active carbohydrate moieties (ACM) may be synthetically produced.

The immunologically active carriers (IAC) of the immunogenic product of the invention preferably derive from polypeptides.

In a preferred embodiment of the invention said polypeptide is tetanus toxoid, diphtheria toxoid, cholera subunit B or Protein D from H. influenzae.

The invention also comprises the use of an immunogenic product according to the invention in human or animal vaccines.

Further, the invention comprises vaccines in which the immunizing component is an immunogenic product according to the invention, and vaccine mixtures which comprise at least two different vaccines according to the invention.

The vaccines may additionally comprise other components approved by the medical authorities for use in vaccines, such as adjuvants.

The invention will be further illustrated by the following non-limiting examples.

EXAMPLE 1

Preparation of thioethylamine derivative of *Salmonella typhimurium* O-polysaccharide.

A *Salmonella typhimurium* octasaccharide (4.1 μmole; 7.5 mg) was dissolved in 1 ml of 0.6 NH$_4$Cl (Merck), and then 20 mg of NaCNBH$_3$ was added during stirring at room temperature. After six days the amine-containing derivative was desalted by gel permeation chromatography on BioGel P-2 (BioRad) and freeze-dried. The *Salmonella typhimurium* octasaccharide derivative was then dissolved in 0.5 ml of 0.1 M sodium bicarbonate buffer (pH 8.2). A 10 molar excess of 2-iminothiolane (Aldrich, Steinheim, Germany) and 5 mg of dithiothreitol were added, and the reaction mixture was stirred for 10 hours at room temperature. The reaction mixture was then subjected to gel permeation chromatography on a Bio-Gel P-2 (BioRad,Sweden) column (1.5×20 cm, eluted with 25 mM pyridinium acetate buffer (pH 5.2). The fractions obtained were measured for their carbohydrate content with the aid of the phenol-sulfur method, and for their thiol groups with 5,5'-dithio-bis-(2-nitrobensoic acid) (Pierce, Inc., Rockford, Ill., USA). The carbohydrate-containing fractions proved to coincide with the thiol-containing fractions in the expected molar proportions, and therefore it could be established that the reaction had proceeded in an equimolar way. These fractions were pooled and concentrated by evaporation in vacuum, followed by blowing nitrogen on top of the concentrated octasaccharide derivative.

Preparation of bromoalkylated tetanus toxoid

N-hydroxysuccinimide bromoacetate (Sigma Inc., St. Louis, Mo., USA) (5 mg) was dissolved in 0.4 ml of 0.1 M sodium bicarbonate buffer (pH 8.3). To this solution 2.5 mg tetanus toxoid dissolved in 1.0 ml of 0.1 M sodium bicarbonate buffer (pH 8.3) was added during stirring. The reaction was allowed to proceed at room temperature (24° C.) for 8 hours. Then the reaction mixture was subjected to gel permeation chromatography on a Sephadex G-25 (PD-10) (Pharmacia, Uppsala, Sweden) column eluted with 0.1 M sodium bicarbonate buffer (pH 8.3). Fractions containing the desired product were pooled.

Preparation of tetanus toxoid- Salmonella octasaccharide conjugate

The bromoalkylated tetanus toxoid (1 mg) in 1.0 ml of 0.1 M sodium bicarbonate buffer (pH 8.3) was mixed and stirred with 5 mg of the mercaptobutyr-imidyl derivative of the octasaccharide dissolved in 0.1 M sodium bicarbonate buffer (pH 8.3). The reaction was allowed to continue for 24 hours at room temperature (24° C.) under nitrogen. The resulting conjugate was then dialyzed against saline solution. Finally, the conjugate was freeze-dried, and measurements of carbohydrate content and protein content, respectively, showed that the resulting conjugate had a substitution of 17.5 moles of carbohydrate/ mole of tetanus toxoid, in average. The conjugate was further characterized by polyacrylamide gel electrophoresis on Pharmacia Phast System (Pharmacia, Uppsala, Sweden), which indicated that the conjugate had a migration which coincides as expected with a degree of substitution of approximately 15–20 moles of carbohydratelmole tetanus toxoid.

EXAMPLE 2

The *Haemophilus influenzae* type B (HiB) capsular polysaccharide (15 mg) was fragmented by oxidation in 0.02 M sodium metaperiodate (4 ml) for 30 minutes at 4° C. The reaction was stopped by addition of 20 µl of ethylene glycol and the HiB oligosaccharide (HiB-OLS) was isolated by gel permeation chromatography in BioGel P-2. The molecular weight of the HiB-OLS obtained was 1.1 kDa as indicated by chromatography on BioGel P-2 column calibrated with dextrans. The HiB-OLS (12 mg) was freeze-dried and dissolved in 0.5 ml of 0.4 M ammonium chloride containing 5 mg of sodium cyanoborohydride. The mixture was agitated for 6 days at 37° C. Aminated HiB-OLS was isolated on BioGel P-2 column eluted with pyridinium acetate buffer, freeze-dried, and dissolved in 0.5 ml of 0.1 M bicarbonate buffer, pH 8.3. Solid 2-iminothiolane hydrochloride (9 mg) was added to the stirred HiB-OLS solution and reaction was continued for 6 hours at room temperature. The mercapto-butyrimidate derivative of HiB-OLS was isolated by chromatography in BioGel P-2. The freeze-dried derivative was dissolved in 2 ml of 0.1 M bicarbonate—2 mM EDTA, pH 8.3.

Purified protein D from *H. influenzae* (Janson et. al., Infect. Immunity; 59, 119; 1991) was dissolved in 1 ml of 0.1 M bicarbonate, pH 8.3 (5 mg/ml). N-hydroxysuccinimide ester of bromoacetic acid (3 mg) was dissolved in 50 µl of dimethylformamide (DMF) and added to the stirred protein D solution. The pH was brought to 8.3 and stirring was continued for 2 hours. The bromoacetylated protein D was separated from the excess of reagents by dialysis against distilled water, and concentrated by ultrafiltration.

The bromoacetylated protein D solution in 0.1. M bicarbonate—2 mM EDTA (4.7 mg in 0.5 ml) was added dropwise to the stirred solution of thiolated HiB-OLS, pH was adjusted to 8.3, and the reaction was carried out for 24 hours at room temperature under nitrogen. Progress of the coupling reaction was monitored with SDS-PAGE in 4–15% polyacrylamide gradient gels (Phast System, Pharmacia). The reaction was terminated by addition of 20 µl of 2-mercapto-ethanol and the conjugate was purified from the excess of reagents by extensive dialysis against distilled water. The carbohydrate and protein analysis of the resulting HiB(OLS)-TTd conjugate revealed a degree of substitution of 6 moles of carbohydrate/mole protein.

EXAMPLE 3

A completely synthetic amino derivative of ribosyl ribitol phosphate decamer ($RRP_{10}$) was dissolved in 0.1 M bicarbonate, pH 8.3 (5 mg in 1 ml). Solid 2-iminothiolane hydrochloride (2.3 mg) was added to the stirred $RRP_{10}$ solution. After 6 hours at room temperature the thiolated $RRP_{10}$ was purified on a BioGel P-2 column, freeze-dried, and next dissolved in 0.4 ml of 0.1 M bicarbonate, pH 8.3.

Bovine serum albumin (BSA) was dissolved in 0.1 M bicarbonate (1.5 mg in 1 ml), the N-hydroxysuccinimide ester of bromoacetic acid in DMF (1.2 mg in 30 µl) was added, pH was adjusted to 8.3, and the mixture was stirred for 2 hours at room temperature. The bromoacetylated BSA was isolated on a PD-10 column eluted with 0.1 M bicarbonate—2 mM EDTA, pH 8.3.

The bromoacetylated BSA (1.2 mg in 0.2 ml) was added dropwise to the solution of the thiolated $RRP_{10}$, and stirred for 18 hours under nitrogen. The reaction was stopped with 20 µl of 2-mercaptoethanol. The $RRP_{10}$-BSA conjugate was purified from the unbound oligosaccharide and other reagents by repeated washing in ultrafiltration cell (cut-off 30 kDa) followed by extensive dialysis against distilled water. Degree of substitution of the conjugate was 5 moles carbohydrate/mole protein.

EXAMPLE 4

The pneumococcal polysaccharide type 14 (PnPs14) (obtained from ATCC No 77217, prepared under GMP) was dissolved in 2 ml of distilled water (20 mg/ml) and fragmented by sonication, using repeated cycle of 10 min impulse and 3 min rest. After thirty cycles (total of 5 hours) the molecular weight of the polysaccharide decreased to an average of 50 kDa, as indicated by chromatography in Sephacryl S-300. The degraded PnPs14 was dialyzed and freeze-dried. The recovered PnPs14 (32 mg) was dissolved in 1 ml of 0.4 M ammonium chloride containing 10 mg of sodium cyanoborohydride and stirred for 4 days at 37° C. Aminated PnPs14 was separated from the excess of reagents by chromatography on BioGel P-2 column, freeze-dried, and dissolved in 1 ml of 0.1 bicarbonate buffer, pH 8.3. Solid 2-iminothiolane hydrochloride (1.7 mg) was added to the PnPs14 solution and the mixture was stirred for 6 hours at room temperature. The mercaptobutyr-imidyl derivative of PnPs14 was next isolated by column chromatography on BioGel P-2 and freeze-dried.

Tetanus toxoid (TTd; 2 mg) (obtained from Statens Seruminstitut, Copenhagen, Denmark) was dissolved in 1 ml of 0.1 M bicarbonate, pH 8.3, and the N-hydroxysuccinimide ester of bromoacetic acid in DMF (1.8 mg in 10 µl) was added. The pH of the reaction mixture was adjusted to 8.3 and the mixture was stirred for 1 hour at room temperature. The bromoacetylated TTd was isolated by chromatography on PD-10 column (Pharmacia) eluted with 0.1 M bicarbonate—2 mM EDTA, pH 8.3, and concentrated to 0.5 ml by ultrafiltration.

The derivatized PnPs14 (30 mg) was dissolved in 1.5 ml of 0.1 M bicarbonate—2 mM EDTA, pH 8.3, and the bromoacetylated TTd solution was added dropwise during stirring. The pH was adjusted to 8.3 and stirring was continued for 24 hours at room temperature under nitrogen. The coupling reaction was monitored by SDS-PAGE 4–15% polyacrylamide gradient gels (Phast System, Pharmacia). The unreacted bromoacetyl groups were blocked by addition of 20 µl of 2-mercaptoethanol. Ammonium sulphate was added to 0.8 M, and pH was adjusted to 6.5. The mixture was applied onto Butyl-Sepharose (Pharmacia, Uppsala, Sweden) column, the uncoupled PnPs14 and the excess of reagents were removed by washing with 0.8 M ammonium sulphate in 20 mM phosphate buffer, pH 6.5, and the PnPs14-TTd conjugate was eluted with a pulse of 20 mM phosphate buffer. Analysis of the carbohydrate and protein content of the conjugate indicated a degree of substitution of 4 moles carbohydrate/mole protein.

Pneumococcal polysaccharide type 23F (ATCC No 2009269) was used for conjugation to tetanus toxoid according to the same protocol, resulting in the PnPs23F-TTd conjugate.

PREPARATION OF THE PNEUMOCOCCAL CONJUGATE VACCINE

Freeze-dried PnPs14-TTd and PnPs23F-1Td conjugates were dissolved in 3.32 ml of 0.9% sodium chloride at concentration 1.51 µg of conjugate saccharide/ml, 1.68 ml of 3% aluminium hydroxide adjuvant (Superfos Biosector, Denmark) was added and the conjugate was absorbed on the adjuvant gel by rotation for 1 hour at room temperature. Resulting vaccine preparaton contained 4 µg of conjugate polysaccharide/ml and 1% aluminium hydroxide adjuvant. Control vaccine preparations containing plain polysaccharides were prepared in the same way.

IMMUNIZATION PROTOCOLS

Eight-week old female outbred NMRI mice were immunized subcutaneously with 0.25 ml of either PnPs14-TTd or PnPs23F-TTd conjugate vaccine (1 µg based on carbohydrate content in vaccine/dose) adsorbed on the aluminium hydroxide adjuvant (5 mice in each group). Control mice were immunized in the same way with either plain Ps14 or plain Ps23F. Booster dose (1 µg based on carbohydrate content) was administered subcutaneously on day 28. Mice were bled from supraorbital plexus every 7 days after primary and booster immunizations. Serum was and stored at —20° C., until analyzed. The serum antibody titers were determined by ELISA (enzymed linked immunosorbent assay).

ELISA

Microtiter plates (Nunc, Denmark) were incubated for 18 hours at +4° C. with 0.1 ml of the relevant pneumococcal polysaccharide dissolved in 0.1 bicarbonate, pH 8.6 (10 µg polysaccharide/ml). The plates were blocked with 2% BSA in PBS- 0.2% sodium azide for 1 hour at 37° C. and washed three times with 0.05% Tween 20–0.9% sodium chloride. The mice sera were diluted serially in 2% BSA—0.05% Tween—PBS and were applied onto the plates for 1 hour at 37° C. The plates were washed with Tween—PBS and incubated with either 2000-fold diluted rabbit anti-mouse IgG—alkaline phosphatase conjugate or rabbit antimouse IgM—alkaline phosphatase conjugate, for 1 hour at 37° C. After Tween—PBS wash the p-nitrophenyl phosphate solution (1 mg/ml) in 1 M diethanolamine buffer—0.5 M magnesium chloride, pH 9.8, was added, and the absorbance was read after 20 minutes at 405 nm in Titertek Multiscan reader (EFALAB, Finland).

RESULTS OF IMMUNIZATION EXPERIMENTS

The primary (3 weeks) and secondary (6 weeks) IgG and IgM responses in NMRI mice immunized with PnPs14-TTd and PnPs23F-TTd conjugates are shown in Table 1 and Table 2.

TABLE 1

IgG and IgM titers in NMRI mice immunized with PnPs14-TTd conjugate or plain polysaccharide. Mean titer ± S.E.M. is shown.

|  | IgG titer | | IgM titer | |
| --- | --- | --- | --- | --- |
|  | PnPs14-TTd | PnPs 14 | PnPs14-TTd | PnPs 14 |
| Preimmune serum | 5 ± 2 | 2 ± 2 | 77 ± 37 | 105 ± 30 |
| 3 weeks | 20369 ± 5032 | 152 ± 117 | 2306 ± 614 | 179 ± 24 |
| 6 weeks | 105817 ± 32230 | 13 ± 11 | 2991 ± 795 | 217 ± 62 |

TABLE 2

IgG and IgM titers in NMRI mice immunized with PnPs23F-TTd conjugate or plain polysaccharide. Mean titer ± S.E.M. is shown.

|  | IgG titer | | IgM titer | |
| --- | --- | --- | --- | --- |
|  | PnPs23F-TTd | PnPs23F | PnPs23F-TTd | PnPs 23F |
| Preimmune serum | 0.1 ± 0.1 | 0.1 ± 0.1 | 11 ± 6 | 2 ± 1 |
| 3 weeks | 692 ± 220 | 0.2 ± 0.1 | 492 ± 43 | 94 ± 44 |
| 6 weeks | 15951 ± 9731 | 1.4 ± 1.2 | 444 ± 120 | 153 ± 54 |

In conclusion, both 23F and the 14 pneumococcal capsular conjugate vaccines induced very strong and boostable IgG responses. As expected neither of the plain polysaccharides induced any significant increase in IgG titers. The IgM responses to the conjugates were, as expected, less pronounced, but were considerably higher than the ones obtained using the plain polysaccharides. This demonstrates that the covalent conjugation, according to the invention, of the different PnPs to the protein carrier (TTd) is a feasible way of obtaining strongly immunogenic PnPs preparations which, unlike the plain polysaccharides, induce strong T helper cell-dependent responses and also immunological memory. Such immunogenic preparations according to the invention are needed for efficient vaccines for immunologically immature children and immunosuppressed adults.

What is claimed is:

1. A method of producing an immunogenic product consisting of antigenically active carbohydrate moieties (ACM) which are each covalently coupled via identical divalent bridge groups to immunologically active carriers (IAC) containing amino groups, wherein said divalent bridge group has the following structural formula

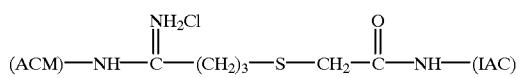

which comprises the steps of reductive amination of antigenically active carbohydrate moieties (ACM) to introduce amino groups on said moieties (ACM—NH$_2$), followed by thiolation of said amino groups with iminothiolane

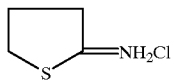

whereupon the so produced thiolated products are covalently coupled to immunologically active carriers (IAC) containing amino groups activated by treatment with N-hydroxysuccinimide bromoacetate, to produce said immunogenic product;

with the provisos that said antigenically active carbohydrate moieties are not T helper cell dependent and said immunologically active carriers comprise T cell epitopes.

2. An immunogenic product consisting of antigenically active carbohydrate moieties (ACM) which each are covalently coupled via identical divalent bridge groups to immunologically active carriers (IAC) containing amino groups, wherein said divalent bridge group has the following structural formula

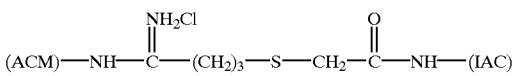

with the provisos that said antigenically active carbohydrate moieties are not T helper cell dependent and said immunologically active carriers comprise T cell epitopes.

3. The immunogenic product according to claim 2, wherein said antigenically active carbohydrate moieties (ACM) are obtained from bacterial O-poly-saccharides and/or capsular Vi-polysaccharide.

4. The immunogenic product according to claim 3, Wherein said saccharides are obtained from Salmonella serotypes BO and/or DO.

5. The immunogenic product according to claim 2, wherein said antigenically active carbohydrate moieties (ACM) are obtained from *Streptococcus pneumoniae* capsular polysaccharides.

6. The immunogenic product according to claim 2, wherein said antigenically active carbohydrate moieties (ACM) are obtained from *Haemophilus influenzae* capsular polysaccharides.

7. The immunogenic product according to claim 5, wherein said antigenically active carbohydrate moieties (ACM) are synthetically produced.

8. The immunogenic product according to claim 2, wherein said immunologically active carrier (IAC) is obtained from a polypeptide.

9. The immunogenic product according to claim 8, wherein said polypeptide is tetanus toxoid.

10. The immunogenic product according to claim 8, wherein said polypeptide is Protein D obtained from *Haemophilus influenzae*.

11. An immunogenic composition which comprises an immunizing component and an adjuvant wherein said immunizing component is an immunogenic product according to claim 2.

12. A method of eliciting an immune response in an animal which comprises administering the product of claim 2 to said animal.

13. An immunogenic product which is mixture of at least two different immunogenic components defined by claim 2 wherein said at least two different immunogenic components differ from another by the identity of said antigenically active carbohydrate moieties.

* * * * *